(12) United States Patent
Ka et al.

(10) Patent No.: US 9,393,226 B2
(45) Date of Patent: Jul. 19, 2016

(54) USE OF OSTHOLE FOR TREATING FOCAL SEGMENTAL GLOMERULOSCLEROSIS

(71) Applicant: National Defense Medical Center, Taipei (TW)

(72) Inventors: Shuk-Man Ka, Taipei (TW); Ann Chen, Taipei (TW); Kuo-Feng Hua, I-Lan (TW); Kuo-Ping Chao, Chiayi County (TW); Shun-Min Yang, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 14/693,570

(22) Filed: Apr. 22, 2015

(65) Prior Publication Data
US 2015/0297560 A1    Oct. 22, 2015

(30) Foreign Application Priority Data

Apr. 22, 2014    (TW) .............................. 103114582 A (51) Int. Cl.
*A61K 31/37*    (2006.01)
*A61K 45/06*    (2006.01)

(52) U.S. Cl.
CPC ................. *A61K 31/37* (2013.01); *A61K 45/06* (2013.01)

(58) Field of Classification Search
None
See application file for complete search history.

(56) References Cited

PUBLICATIONS

Schachter, et al., Nephron., 82:300 (1999).*
Tsai, et al., Free Radical Biology and Medicine, 50:1503 (2011).*
Liao, P-C, et al., J. Agri. Food. Chem., 58:10445 (2010).*

* cited by examiner

*Primary Examiner* — Michael Barker
(74) *Attorney, Agent, or Firm* — WPAT, P.C., Intellectual Property Attorneys; Anthony King (57) ABSTRACT

The present invention relates to use of osthole for manufacturing a composition for treating focal segmental glomerulosclerosis (FSGS). Particularly, the present invention discloses that osthole is effective in treating focal segmental glomerulosclerosis (FSGS), which can alleviate various symptoms and signs of FSGS, including proteinuria, renal fibrosis, glomerular epithelial hyperplasia lesion (EPHL), and macrophage/lymphocyte infiltration in the kidney, etc.

3 Claims, 11 Drawing Sheets

USE OF OSTHOLE FOR TREATING FOCAL SEGMENTAL GLOMERULOSCLEROSIS

RELATED APPLICATIONS

This application claims the benefit of Taiwanese Patent Application No. 103114582, filed on Apr. 22, 2014, the entire content of which is incorporated herein by reference.

TECHNOLOGY FIELD

The present invention relates to use of osthole for treating focal segmental glomerulosclerosis.

BACKGROUND OF THE INVENTION

Focal segmental glomerulosclerosis (FSGS) is a kidney tissue-lesion disease where glomerular sclerosis occurs the kidney. The clinical manifestation of which are nephrotic syndromes, comprising severe proteinuria, hypertension, hypoalbuminemia and hematuria etc. (Cattran D C, Rao P. *American Journal of Kidney Disease,* 21(3):344-9, 1998; Chun M J et al., *Journal of the American Society of Nephrology,* 15:2169, 2004; Rydel J J et al., *American Journal of Kidney Disease,* 25(4):534-42, 1995). During the initial phase of the disease, the symptoms include thickening of the glomerular basement membrane, increasing of glomerular extracellular matrix, appearance of deposition of hyaline masses in blood vessels, and finally the formation of scar tissues composed mainly of collagen, accompanied by accumulation of foam cells on the capillary wall, capillary collapse, hyperplasia and hypertrophy of visceral epithelial cells, and podocyte fusion; the sclerotic portion expands gradually with the progression of the disease (D'Agati V D. Curr Opin Nephrol Hypertens 17(3):271-81, 2008; Hodgin J B et al., American Journal of Clinical Pathology, 177(4): 1674-86, 2010; and Thomas D B., The Archives of Pathology and Laboratory Medicine. 133(2):217-23, 2009). Podocytes mainly distribute on the glomerular basement membrane, their function being the filtration of blood. Super resolution microscopy is currently able to observe the damaged condition of the podocytes in the glomerulus of a FSGS patient, which is considered as one of the main reasons of the sclerosis of the glomerulus (Kriz W et al., *Kidney International.* 54(3): 687-97, 1998. Pagtalunan M E et al. *The Journal of Clinical Investigation.* 99(2):342-8, 1997. Wiggins J E et al. *Journal of the American Society of Nephrology.* 16(10):2953-66, 2005. Yang H C et al., Kidney International. 69(10):1756-64, 2006).

The number of focal segmental glomerulosclerosis (FSGS) patients increase each year in various countries. However, its pathological mechanism is not yet fully understood. Possible causes are other types of nephritis, such as focal proliferative nephritis, vasculitis, lupus nephritis, kidney transplant, or toxic damage (Bahiense-Oliveira M et al. *Clinical Nephrology.* 61:90-7, 2004. D'Agati V. *Seminars in Nephrology.* 23:117, 2003). Clinically, it is treated by cytotoxic drugs (e.g. cyclophosphamide), immunosuppressants (e.g. cyclosporine, Mycophenolate Mofetil), non-steroidal anti-inflammatory drugs (NSAIDs), vasodilators, or solely by corticosteroids (e.g. prednisolone). However, only 20%-40% of the patients are responsive to treatment by steroids, and it is only effective after long-term administration. Even after the treatment by steroids, there is still a chance for the disease to develop to an end-stage renal disease in a patient (Beşbaş N et al., Turkish *Journal of Pediatric.* 52(3):255-61, 2010. Daskalakis N, Winn M P. *Cellular and Molecular Life Sciences.* 63(21):2506-11, 2006. Gipson D S et al., *Kidney International.* 80 (8):868-78, 2011. Daskalakis N, Winn M P. *Cellular and Molecular Life Sciences.* 63(21):2506-11, 2006. Gipson D S et al., *Kidney International.* 80 (8):868-78, 2011. Kanjanabuch T et al, *Journal of The Medical Association of Thailand.* 2:S262-79, 2006). In addition, these drugs often produce harmful side-effects, such as drug resistance and renal toxicity, which generates greater harm to the human body, and there are also issues such as recurring after discontinuance of use of the drug.

Osthole, its nomenclature being 7-methoxy-8-(3-methyl-but-2-enyl)-2-chromanone, and its molecular formula being $C_{15}H_{16}O_3$, has the following structure:

Osthole can be extracted from the seeds of the Apiaceae genus plant *Cnidium monnieri*, which is already known to possess anti-microbial-infection, anti-proliferation and anti-allergic effects. However, no prior art has disclosed its renal protective effects of osthole in treating or relieving various symptoms of focal segmental glomerulosclerosis.

BRIEF SUMMARY OF THE INVENTION

The present invention is based on the unexpected finding that osthole is effective in alleviating the symptoms of focal segmental glomerulosclerosis (FSGS). Therefore, the present invention provides a new approach for treatment of focal segmental glomerulosclerosis (FSGS) in a subject.

In particular, the present invention provides a method for treating focal segmental glomerulosclerosis (FSGS) in a subject in need thereof, which comprises administering a therapeutically effective amount of osthole to the subject.

Specifically, the method for treating of the present invention is effective to reduce one or more symptoms of FSGS in the subject, including but not limited to expansion of glomerular extracellular matrix, deposition of hyaline masses, fibrosis of renal tissues, glomerular epithelial hyperplasia lesions (EPHLs) and lymphocyte infiltration. Also, the method for treating of the present invention is effective to reduce proteinuria or hematuria or lower serum urea nitrogen level or serum creatinine level in the subject.

In some embodiments, the osthole is administered in combination with one or more therapeutic agents for treating focal segmental glomerulosclerosis known in the art, including but not limited to corticosteroid drugs, non-steriodal anti-inflammatory drugs (NSAIDs), immunosuppressants, cytotoxic drugs and vasodilators.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments which are presently preferred. It should be understood, however, that the invention is not limited to the illustrated preferred embodiments. In the drawings.

DETAILED DESCRIPTION OF THE INVENTION

Unless defined otherwise, all technical and scientific terms used herein have the same meanings as is commonly understood by one of skill in the art to which this invention belongs. If a conflict appears, one should base on this document, including the definitions therein.

As used herein, the articles "a" and "an" refer to one or more than one (i.e., at least one) of the grammatical object of the article. By way of example, "an element" means one element or more than one element.

In the present invention, it is unexpectedly found that osthole is effective in improving or alleviating conditions of focal segmental glomerulosclerosis (FSGS), including expansion of glomerular extracellular matrix, deposition of hyaline masses, fibrosis of renal tissues, glomerular epithelial hyperplasia lesions (EPHLs) and lymphocyte infiltration, and also reducing proteinuria or hematuria or lowering serum urea nitrogen level or serum creatinine level in FSGS animals. It is found that osthole is renoprotective for FSGS which acts via reducing oxidative stress through activation of Nrf2 and its downstream genes involved in potent anti-oxidant pathways, reducing inflammation through NF-κB, and decreasing apoptosis by reducing caspase-9, caspase-3.

Therefore, the present invention provides a therapeutic approach to treat or ameliorate certain pathological and physiological symptoms of FSGS. Specifically, the method of the invention is effective in reducing one or more symptoms of FSGS including expansion of glomerular extracellular matrix, deposition of hyaline masses, fibrosis of renal tissues, glomerular epithelial hyperplasia lesions (EPHLs) and lymphocyte infiltration, in a subject having FSGS. The method of the invention is also effective in reducing proteinuria or hematuria or lowering serum urea nitrogen level or serum creatinine level in a subject with FSGS.

As known in the art, focal segmental glomerulosclerosis (FSGS) is a kidney disease where scaring (sclerosis) occurs in a portion of some (focal) but not all glomeruli, which can be identified by a biopsy of renal tissue. FSGS shows pathological symptoms including glomerular epithelial hyperplasia lesions (EPHLs), a key histopathology index of progression of FSGS, and also peri-glomerular inflammation and glomerular hyalinosis or sclerosis. FSGS also shows renal dysfunction symptoms such as severe proteinuria, hypertension, hypoalbuminemia and hematuria etc. (Cattran D C, Rao P. *American Journal of Kidney Disease,* 21(3):344-9, 1998; Chun M J et al., *Journal of the American Society of Nephrol-* ogy, 15:2169, 2004; Rydel J J et al., *American Journal of Kidney Disease*, 25(4):534-42, 1995). As the progression of the disease, the symptoms include thickening of the glomerular basement membrane, increasing of glomerular extracellular matrix, appearance of glass-like deposits in blood vessels, and then formation of scar tissues composed mainly of collagen, accompanied by accumulation of foam cells on the capillary wall, capillary collapse, hyperplasia and hypertrophy of visceral epithelial cells, and podocyte fusion; the sclerotic portion expands gradually with the progression of the disease (D'Agati V D. Curr Opin Nephrol Hypertens 17(3): 271-81, 2008; Hodgin J B et al., American Journal of Clinical Pathology, 177(4):1674-86, 2010; and Thomas D B., The Archives of Pathology and Laboratory Medicine. 133(2):217-23, 2009).

The present invention is based on the unexpected finding that osthole is effective in treating focal segmental glomerulosclerosis (FSGS). Patients with FSGS present various symptoms including expansion of glomerular extracellular matrix, deposition of hyaline masses, fibrosis of renal tissues, glomerular epithelial hyperplasia lesions (EPHLs) and lymphocyte infiltration, or proteinuria or hematuria, or elevated serum urea nitrogen level or serum creatinine level. The method of the invention is effective in improving any one of these symptoms in patients with FSGS.

In the examples of the present invention, it is found that the following effects can be achieved through the administration of osthole in FSGS animal model experiments: (1) reducing proteinuria and renal function damages, suppressing pathological changes in kidney tissues and reducing collagen IV expression to suppress kidney tissue fibrosis; (2) reducing systemic ROS expression level, increasing the expression of Nrf-2 transcription factor and its downstream gene HO-1, and increasing Gpx activity; (3) suppressing macrophage infiltration and activation of NF-κB pathway, and reducing protein expression of cyclooxygenase-2 (COX-2) and prostaglandin E2 (PGE2); and (4) suppressing the apoptosis pathway in kidney tissues. These results demonstrate that osthole has excellent renaprotective effects in treating or ameliorating the symptoms of focal segmental glomerulosclerosis, and is highly related to the effects in anitoxygenic pathway of NF-κB, reducing NF-κB inflammatory pathway and suppressing apoptosis of kidney tissues.

The osthole used in the present invention has the chemical name of 7-methoxy-8-(3-methylbut-2-enyl)-2-chromanone and the molecular formula of $C_{15}H_{16}O_3$ with the following structure:

Osthole may be obtained commercially or through extraction from natural plant products, including but not limited to *C. monnieri* seeds. It may be extracted by methods well known in the art, (see: J. Agric. Food Chem. 2010, 58, 10445-10451), for example, using methanol as solvent to extract *C. monnieri* seeds (e.g. immerse *C. monnieri* seeds in 95% ethanol for 10 days, repeating 3 times) and purify by chromatography to obtain purified osthole. When osthole is described as isolated or purified in the present invention, it should be understood as not absolutely isolated or purified, but relatively isolated or purified. For example, purified osthole refers to one that is more purified compared to its naturally existing form. In one embodiment, a preparation comprising purified osthole may comprise osthole in an amount of more than 50%, more than 60%, more than 70%, more than 80%, more than 90%, or 100% (w/w) of the total preparation. It should be understood that when a certain number was used herein to show a ratio or dosage, said number generally includes dosages within the range of 10% more and less, or more specifically, the scope of 5% more and less than the number.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom of the disorder, or a progression of the disorder, with the purpose to cure, heal, alleviate, relieve, alter, remedy, ameliorate, improve, or affect the disorder, the symptoms of the disorder, the disabilities induced by the disorder, or the progression of the disorder.

The term "therapeutically effective amount" used herein refers to the amount of an active ingredient to confer a therapeutic effect in a treated subject. For example, an effective amount for treating focal segmental glomerulosclerosis is an amount that can prohibit, improve, alleviate or reduce one or more symptoms such as expansion of glomerular extracellular matrix, deposition of hyaline masses, fibrosis of renal tissues, glomerular epithelial hyperplasia lesions (EPHLs) and lymphocyte infiltration, or reducing proteinuria or blood urea nitrogen or serum creatinine level, in a subject having FSGS. The symptoms may be determined and evaluated using methods known in the art based on various disease progress-related indexes, for example by analyzing the amount of urine protein, blood urea nitrogen or serum creatinine, or by analyzing renal sections. The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the oral dosage of osthole used in the present invention is 1 to 1,000 mg/kg daily, specifically 5 to 500 mg/kg daily, more specifically 10 to 250 mg/kg daily, even more specifically 20 to 175 mg/kg daily. One or more administrations can be done daily depending on the need.

According to the present invention, osthole may be used as an active ingredient for treating focal segmental glomerulosclerosis. In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, osthole or compositions comprising osthole as the active ingredient may be used in treating individuals with focal segmental glomerulosclerosis. Specifically, osthole or compositions comprising osthole as the active ingredient may be administered to individuals with focal segmental glomerulosclerosis or individuals with the risk of acquiring focal segmental glomerulosclerosis so as to prevent occurrence of the disease or improve the symptoms or delay deterioration of the symptoms.

In addition, according to the present invention, osthole or compositions comprising osthole as the active ingredient may be used in combination with existing therapeutic methods or medicaments, such as plasmapheresis or protein adsorption, or pharmaceutical treatment, including but not limited to corticosteroids (such as prednisolone), non-steriodal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors)). In one embodiment, the medicament or therapeutic method used in combination may be used simultaneously (parallel) or sequentially. When medicaments are used in combination, the medicaments may be mixed in the same formula or put in different formulas separately, such as separate capsules, pills, tablets, and injections.

According to the present invention, osthole or compositions comprising osthole as the active ingredient can be directly administered to a subject, or be prepared as medicaments, or added into food as food additives. Osthole does not exhibit cytotoxicity in use, thus can be taken by or added to the diet of a patient, allowing its renoprotective effects of treating or ameliorating the symptoms to be exerted easily.

The present invention is further illustrated by the following examples, which are provided for the purpose of demonstration rather than limitation.

EXAMPLES

1. Materials and Methods

1.1 Mouse FSGS Model and Experimental Protocol

Experiments were performed on 8-week-old female BALB/c mice. The mice were separated into 3 groups at 8-weeks old. One of the groups were injected intravenously with normal saline to be used as normal controls, where the pathological control group and the osthole treated group were intravenously injected with a single dose of adriamycin (0.1 mg/10 g body weight) to induce FSGS, wherein the osthole treated group is intraperitoneally injected with osthole at a daily dose of 30 mg/kg body weight starting from 6 hours before FSGS induction by adriamycin. After intravenous injection of adriamycin, osthole was continuously given to the osthole treated group through intraperitoneal injection with a daily dose of 30 mg/kg body weight until they were sacrificed 28 days after FSGS induction. The pathological control group were given vehicle by intraperitoneal injection in the same fashion. Urine samples were collected in metabolic cages on days 3, 7, 14, and 21. Mice were sacrificed at day 7 or 28 post disease induction. Renal cortical tissues, spleen and serum were collected and stored properly for further analysis.

1.2 Preparation of Osthole (7-methoxy-8-(3-methylbut-2-enyl)-2-chromanone)

Osthole was isolated from the *C. monnieri* seeds (J. Agri. Food Chem. 2010, 58, 10445-40451) by extraction using 95% (v/v) ethanol, saturated and dissolved in ethanol again, then purified by high performance liquid chromatography (HPLC) to obtain purified osthole.

1.3 Analysis of Urine Protein and Renal Function

Mice urine samples were collected by metabolic cages. Proteinuria was first tested with test paper, following the measurement of protein concentration with BCA Protein Assay Kit (PIERCE), where the urinary protein index was illustrated by 24-hour proteinuria (urinary protein concentration/urinary creatinine concentration). In addition, blood was collected through the eye socket, after separation, serum specimen was obtained, which was absorbed into Fuji Ori-Chem Slide and measured by machine (Fuji Photo Film Co., Tokyo, Japan) to read the data.

1.4 Pathologic Evaluation

Renal tissues were formalin-fixed, embedded in paraffin, and sections (4 μm) were prepared and stained with hematoxylin and eosin (H&E). Renal pathology was examined under optical microscope and renal lesions was scored. or EPHLs and sclerosis, at least 50 glomeruli in sections were examined for each mouse.

In addition, immunohistochemistry was also performed. Formalin-fixed and paraffin-embedded renal sections were prepared and incubated with primary antibodies against mouse F4/80 (monocyte/macrophage; Serotec), NF-κB p65 (Cell Signaling Technology, MA., USA), or collagen IV (Southern Biotech, AL, USA) then with biotinylated second antibodies (Dako, Glostrup, Denmark) and avidin-biotin-peroxidase complex (Dako) to amplify the signal. A quantitative image analysis software Pax-it; Paxcam, Villa Park, Ill., USA) was used to analyze the staining results.

1.5 Kidney Tissue Protein Extraction and Western Blot Analysis

Cytoplasmic and nuclear proteins were extracted from renal tissues using a Nuclear Extract Kit (Active Motif, Tokyo, Japan) according to the manufacturer's instructions. Protein extract was separated by electrophoresis and blotted. Target proteins were detected by Western blot analysis using primary antibodies against mouse Nrf2 (Santa Cruz), COX-2 (Santa Cruz), caspase-3 (Cell Signaling Technology, MA, USA), or caspase-9 (Cell Signaling Technology, MA, USA). Antibodies against histone H3 (Cell Signaling, CO, USA) or β-actin (Santa Cruz) were used as internal controls for the nuclear and cytosolic target proteins, respectively. Lastly, secondary antibodies were added and their signals were detected by chemiluminescence.

1.6 Enzyme Linked Immunosorbent Assay

Serum PEG2 and renal HO-1 levels in mice were determined by enzyme linked immunosorbent assay according to the manufacturer's (R&D, U.S.A., Active Motif) instructions.

1.7 Gpx Enzyme Activity Analysis

GPx activity in renal tissues was measured using a commercial glutathione peroxidase assay kit (Cayman, Mich., USA) according to the manufacturer's instructions. Enzymatic activity was represented as a value relative to the protein concentration in glomerular homogenates.

1.8 Reactive Oxygen Species (ROS) Determination

Lucigenin was used to react with the ROS in urine, and detected with Hidex microplate luminometer (Finland), the results were represented as reactive luminescence units (RLU) per 15 min per milligram dry weight (i.e., RLU/15 min/mg dry weight). ROS in kidney tissues were detected with dihydroethidium (DHE), and quantitation was done by determining the ratio of signal positive nucleus/total nucleus in each kidney trans-section.

1.9 Measurement of Apoptosis in Kidney Tissues

TUNEL (Terminal deoxynucleotidyl transferase dUTP nick end labeling) was used for the detection of apoptosis. Kidney sections were prepared by fixing with formalin and embedded in paraffin. A commercially available kit (ApopTaq Plus Perosidase in Situ Apoptosis Detection Kit, Chemicon, USA) was used to mark dogoxigenin-linked dUTPs on DNA breaking ends through UT (Terminal deoxynucloetidyl transferase) enzymes, HRP-linked anti-digoxigenin antibodies were used to amplify the signals, and DAB was used for coloration according to the manufacturer's instructions.

1.10 Statistical Analysis

The results are presented as the mean±SEM. Comparison between two groups was performed using ANOVA or Student's t test. A value of $p<0.05$ was considered statistically significant.

2. Results

2.1 Osthole Ameliorated Pathological Syndromes in Mouse FSGS Model (Evaluation of Proteinuria and Renal Function)

Figure 1:
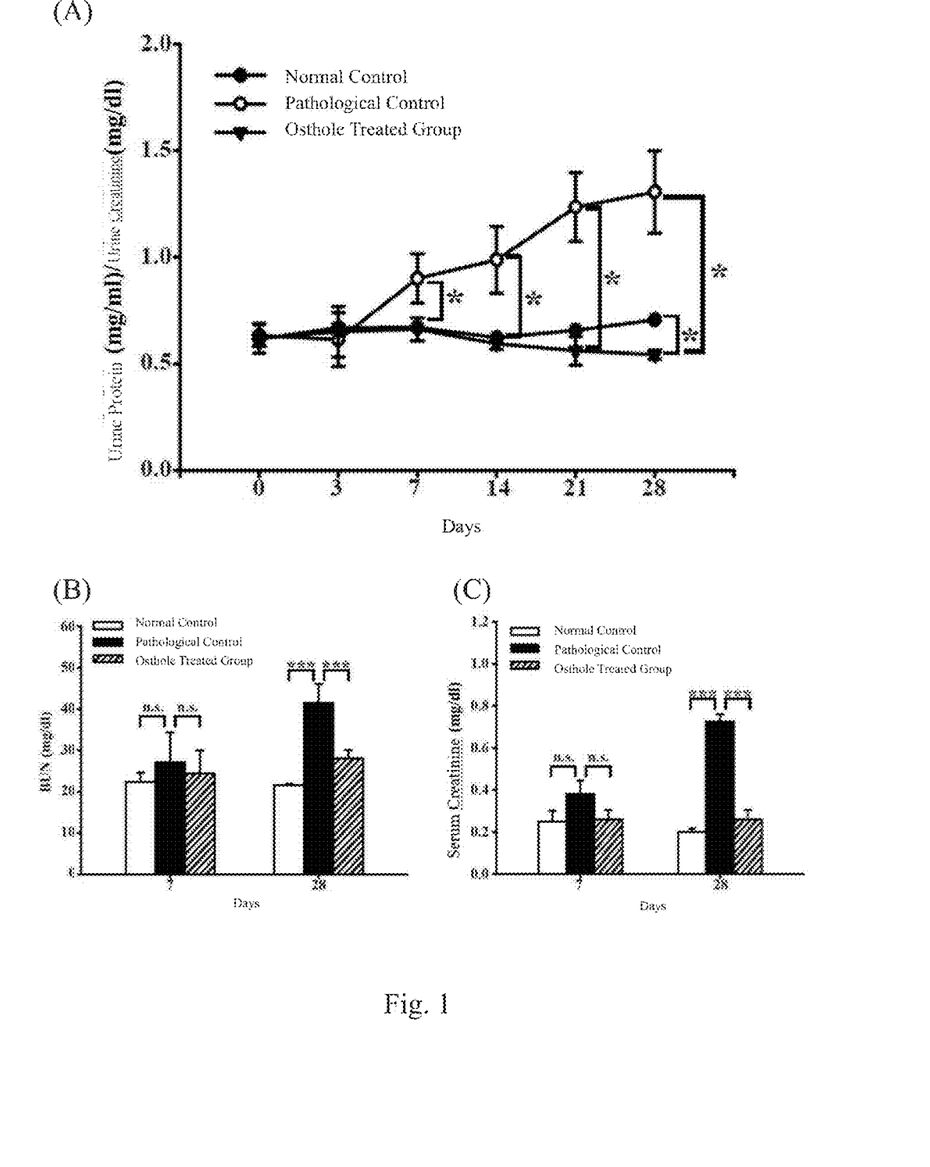
FIG. 1 shows the change of urine protein and renal function, including urine protein/urine creatinine ratio (A), serum blood urea nitrogen (BUN) level (B), and serum creatinine level (C) in osthole treated FSGS mice. $*p<0.05$, $p<0.01$, $*p<0.005$, n.s.=non-significant.

To analyze the effect of osthole on FSGS mice, the proteinuria and renal function index were continuously monitored, for which the results are shown in FIG. 1 (A) to (C). The adriamycin induced FSGS mice showed increase urine protein concentration since the $7^{th}$ day and continued to the $28^{th}$ day. However, such phenomenon in mice treated with osthole can almost be completely suppressed, wherein their urine protein concentration is similar to the normal control group. In addition, analysis of blood urea nitrogen (BUN) and serum creatinine (Cr) showed that the pathological control group had significant increase in BUN and Cr (the $28^{th}$ day), whereas the osthole treated group had lower BUN and Cr concentration, similar to that of the normal control group.

These results show that osthole can significantly lower proteinuria and ameliorate kidney function in FSGS mice.

2.2 Osthole Ameliorates Pathological Change Conditions in FSGS Mice

2.2.1 Histological Changes

Figure 2:
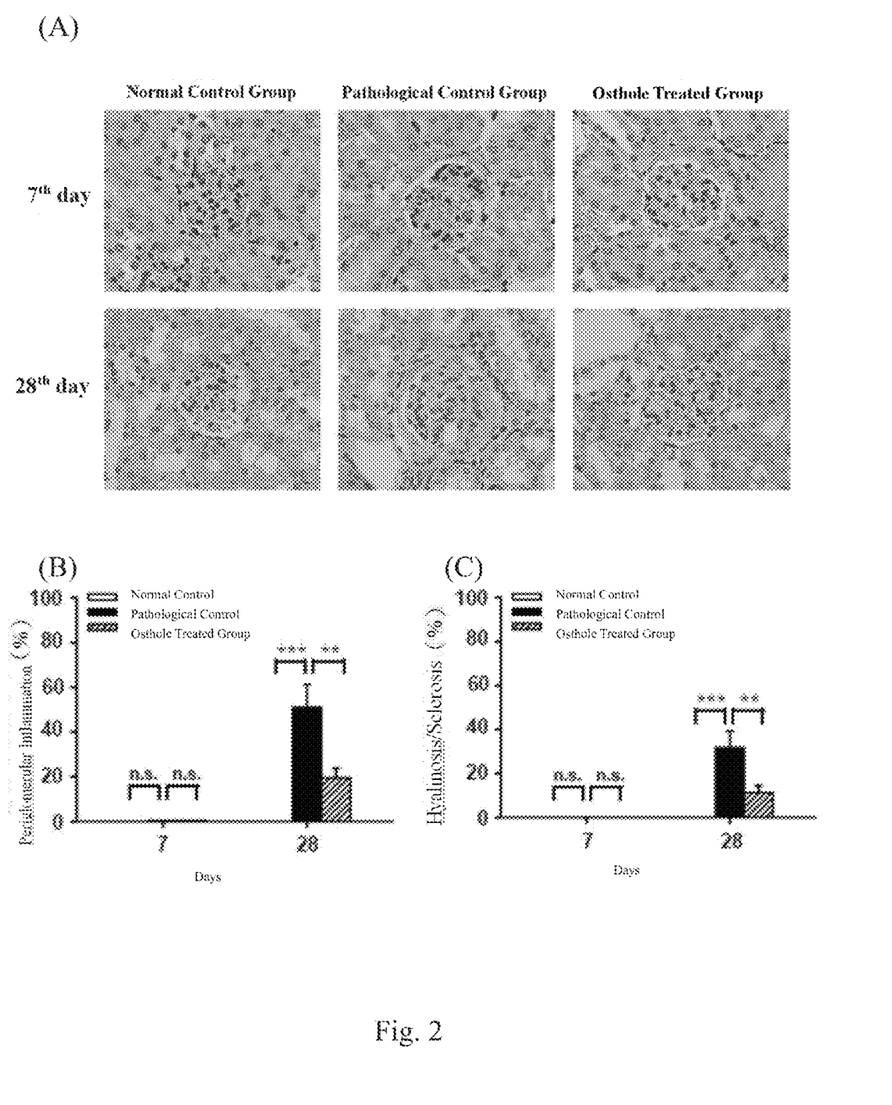
FIG. 2 shows the histomorphological changes in osthole treated FSGS mice, including the staining results (A), the quantitation of mononuclear leukocyte infiltration (B) and the quantitation of glomerular sclerosis (C) of the normal control group, the FSGS disease group (pathological control group), and the FSGS disease osthole treatment group after the $7^{th}$ and the $28^{th}$ day of lesion induction. $*p<0.05$, $p<0.01$, $*p<0.005$, n.s.=non-significant.

Histopathology examination was performed on kidney tissue sections. Starting from the $7^{th}$ day of disease induction, expansion of glomerular extracellular matrix and deposition of hyaline masses in the glomeruli were observed and these effects evolved to obvious sclerotic lesions on the $28^{th}$ day. In addition, on the $28^{th}$ day after disease induction, pathological examination demonstrated that a significant proportion of glomerulus showed EPHL, and peri-glomerular mononuclear leukocyte infiltration (periglomerular region of interstitium) was also largely observed, indicating a progressive pathological status. In comparison, administration of osthole can significantly suppress the disease progression of glomerular sclerosis, as shown in FIGS. 2 (A), (B) and (C).

2.2.2 Evaluation of Renal Fibrosis

Figure 3:
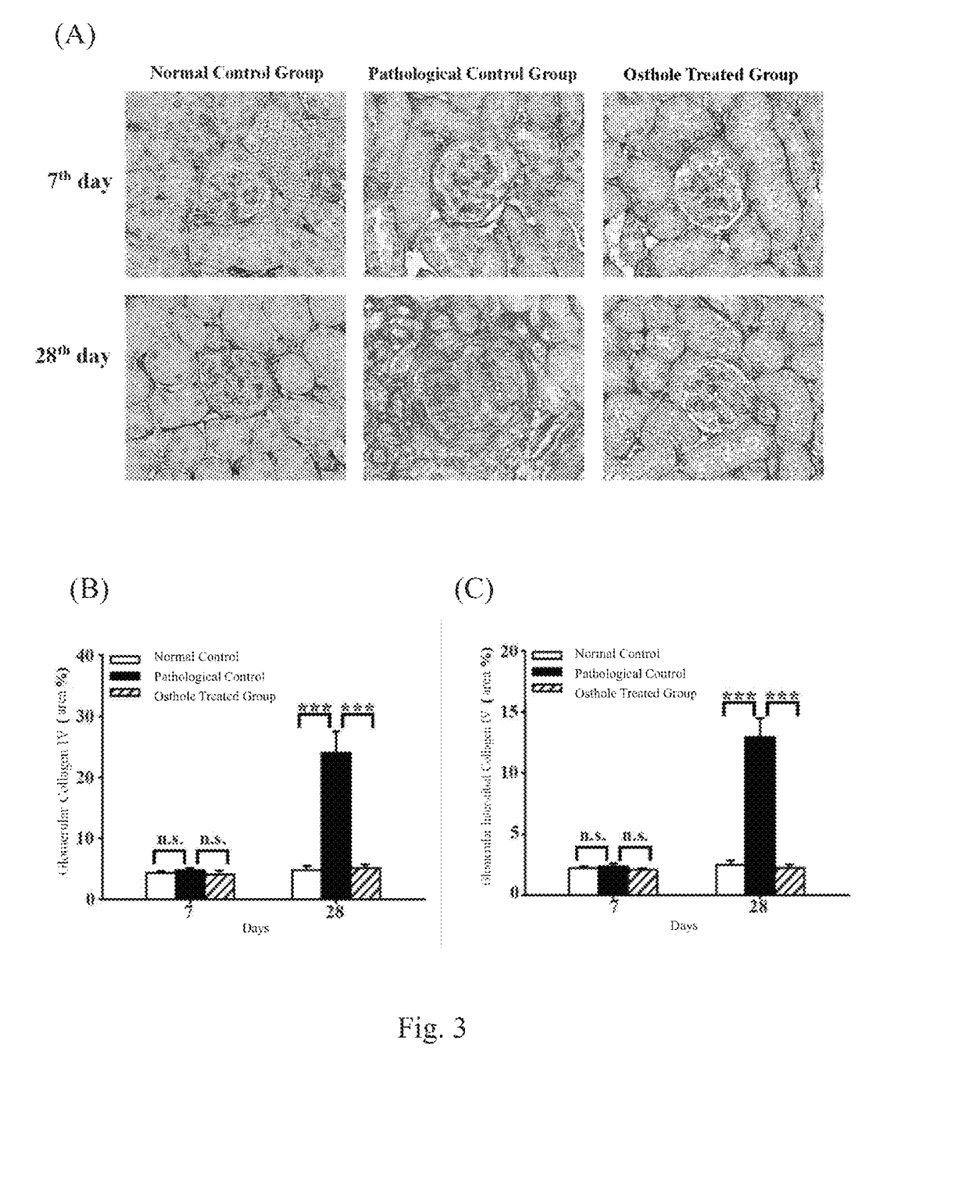
FIG. 3 shows the expression level of collagen IV in kidney tissues of osthole treated FSGS mice, including the staining results (A) and their quantitation (B-C) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.
Figure 4:
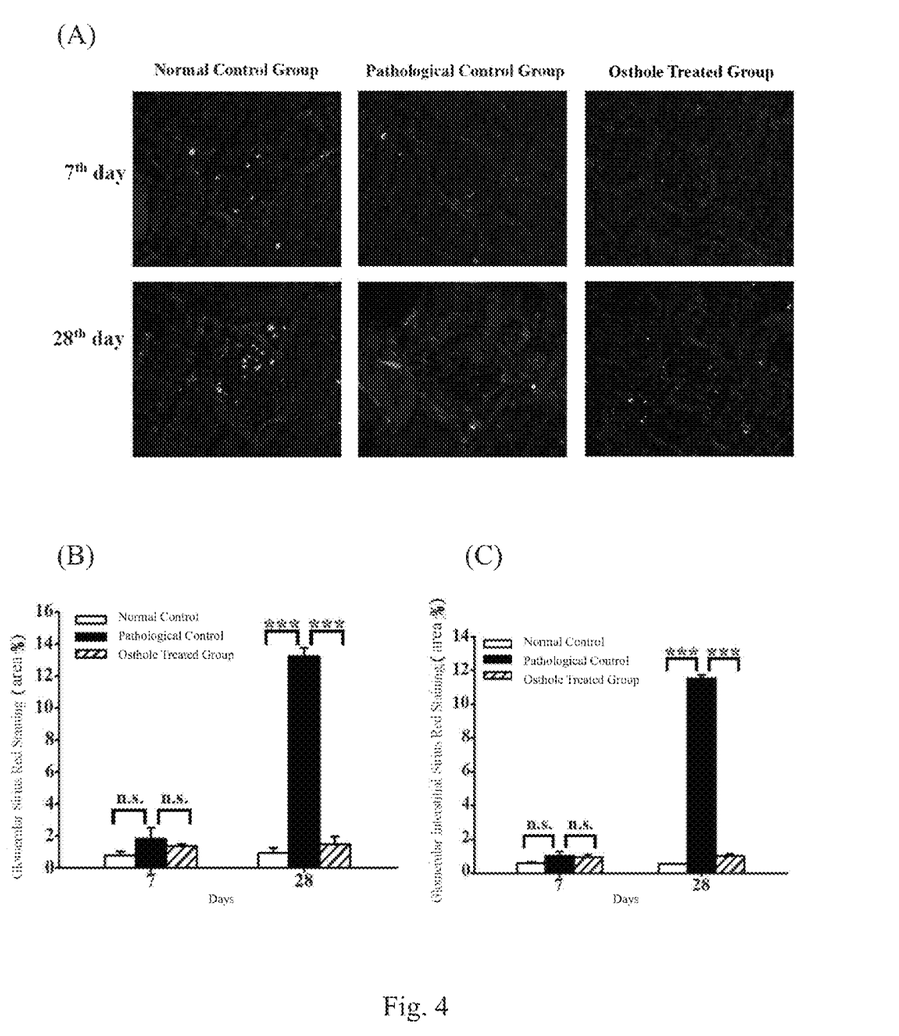
FIG. 4 shows the tissue sclerosis condition in osthole treated FSGS mice (by Sirius Red staining), including the staining results (A) and their quantitation (B-C) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.

Focal segmental glomerulosclerosis (FSGS) is a kidney disease of glomerular sclerosis and fibrosis. Therefore, renal fibrosis was evaluated by using collagen IV immunohistochemistry (IHC) and Sirius red staining. FIGS. 3 (A), (B) and (C) shows the immunostaining results of collagen IV, demonstrating that osthole treatment can significantly suppress collagen IV expression in glomerular tissue, where the expression level is similar to that of the normal control group. On the other hand, as shown in FIGS. 4 (A), (B) and (C), the Sirius red staining shows that after the $28^{th}$ day of disease induction, significant fibrosis phenomenon occurred. In contrast, osthole was able to suppress fibrosis of the renal tissue, similar to the normal control group.

These results demonstrate that osthole can significantly suppress renal tissue fibrosis of FSGS mice.

Figure 5:
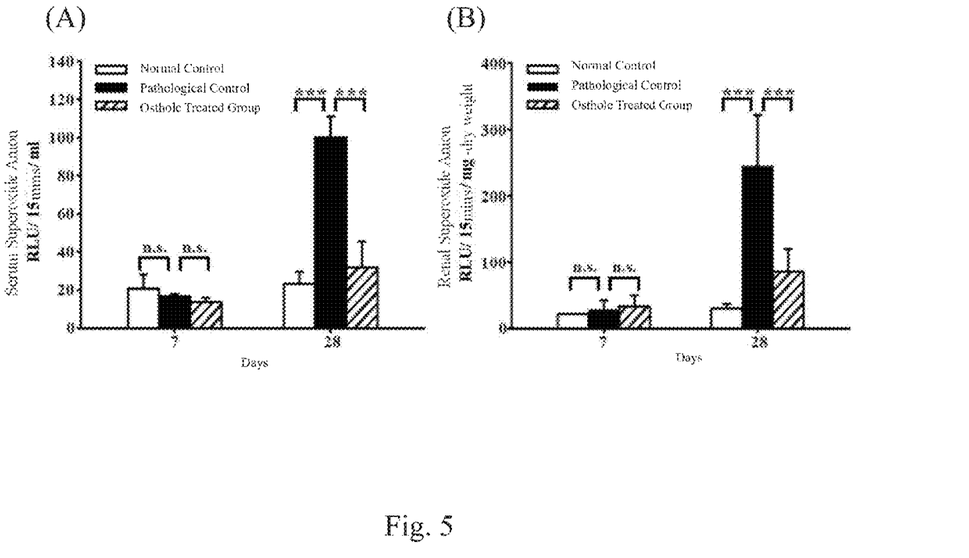
FIG. 5 shows the expression level of reactive oxygen species (ROS) in osthole treated FSGS mice, including the serum ROS expression (A) and kidney ROS expression (B) of the normal control group, the FSGS disease group (pathological control group), and the FSGS disease osthole treatment group after the 7th and the 28th day of lesion induction. RLU=relative light unit, $*p<0.05$, $p<0.01$, $*p<0.005$, n.s.=non-significant.
Figure 6:
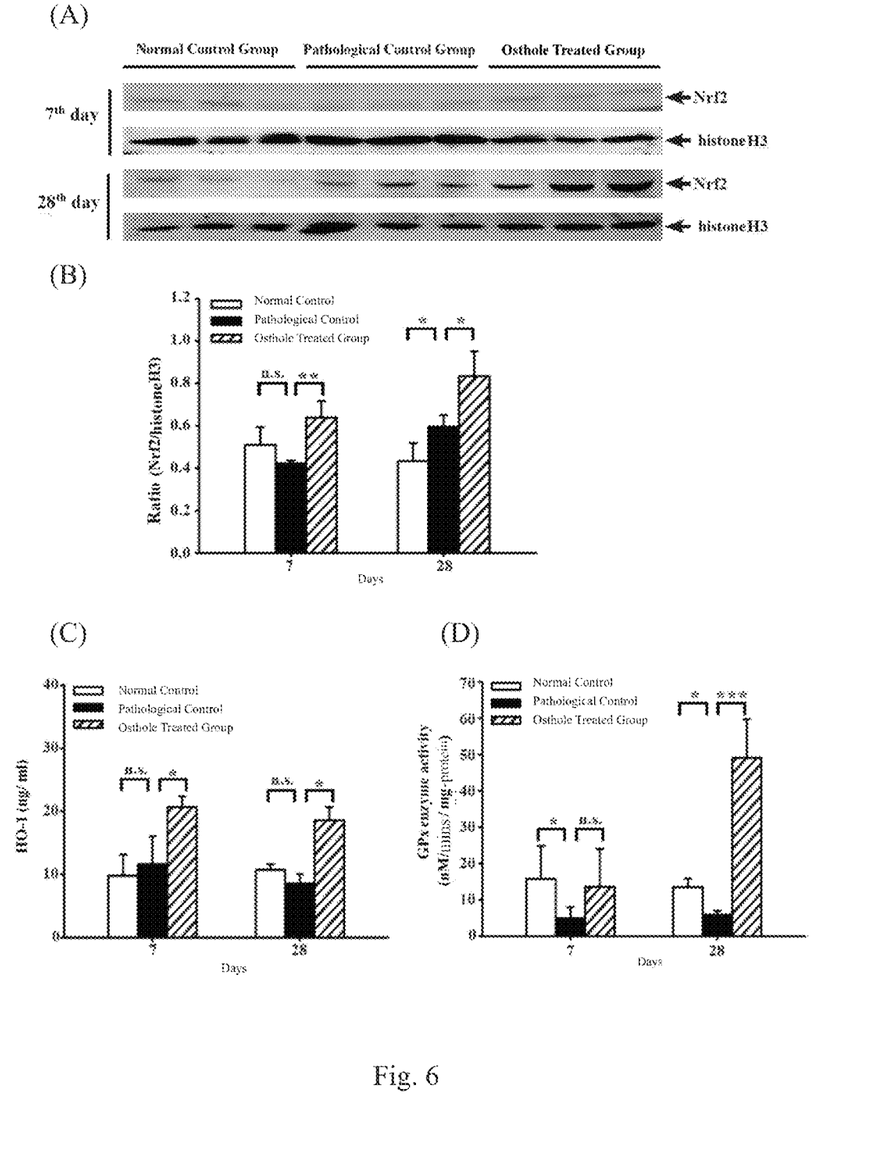
FIG. 6 shows the Nrf2 and HO-1 expression levels and the Gpx enzyme activity in kidney tissues of osthole treated FSGS mice, including the Nrf2 Western blot analysis result (A) and its quantitation (B), the HO-1 Western blot analysis result (C) and its quantitation, and the Gpx enzyme activity (D) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.

2.3 Osthole Reduces Kidney Reactive Oxygen Species (ROS) Through the Nrf2 Pathway To analyze the anti-oxidative activity of osthole, ROS content in serum or kidney tissue were measured, and Western blot analysis was used to analyze the activation of anti-oxidative pathways. As shown in FIGS. 5 (A) and (B), after the $28^{th}$ day of disease induction, large amount of superoxide anion can be detected in the serum and the kidney tissue of the pathological control group, indicating high oxidative stress, wherein the osthole treated mice demonstrated suppressed exhibition of such phenomenon. The activation of anti-oxidative signaling pathway was further analyzed by measuring the Nrf2 translocation into the nucleus, the HO-1 expression level and GPx activity. As shown in FIGS. 6 (A), (B), (C) and (D), it is found that contrary to the pathological control group, administration of osthole can significantly increase the Nrf2 translocation. Also, the GPx activity in kidney tissues of the pathological control group is significantly lowered. Administration of osthole can significantly increase HO-1 expression and GPx activity (FIGS. 5 (A), (B) and (C)).

These results demonstrate that osthole is able to lower the ROS expression in FSGS mice through the Nrf2 pathway.

2.4 Osthole Reduces Inflammatory Cell-Infiltration and Inflammation

Figure 7:
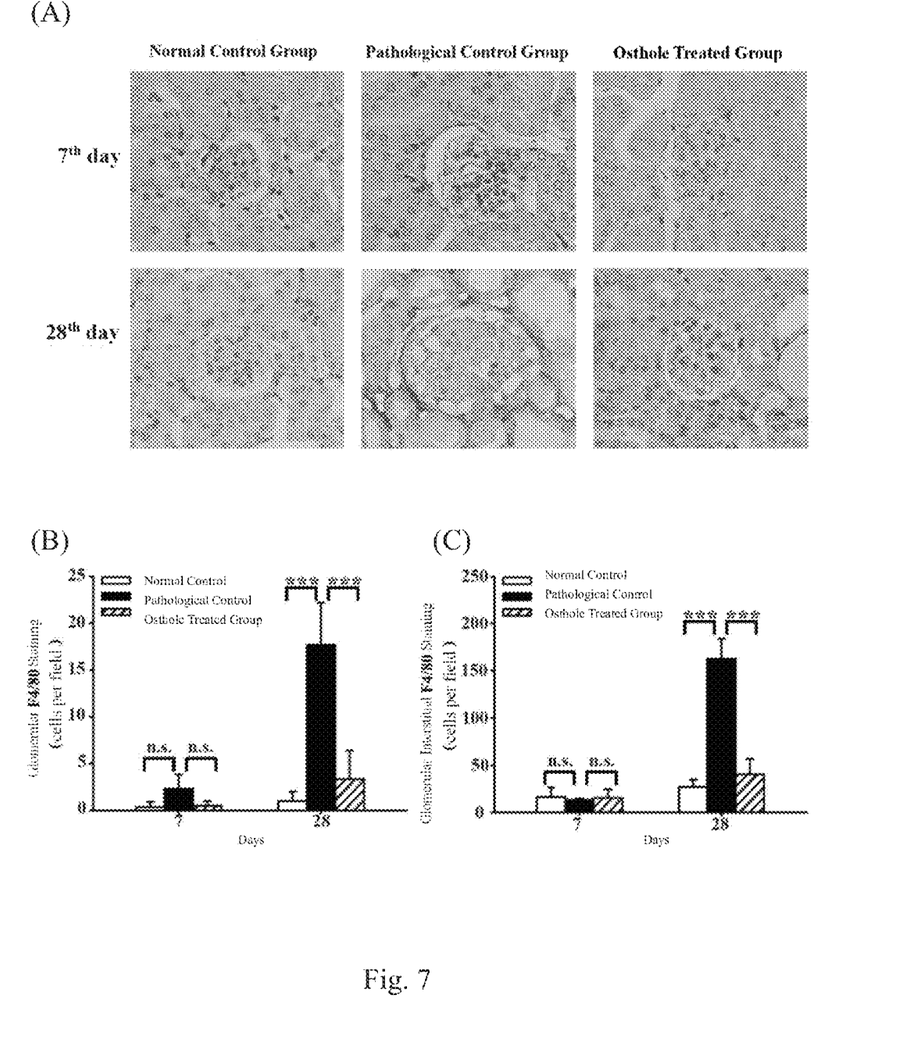
FIG. 7 shows the macrophage infiltration conditions in kidney tissues of osthole treated FSGS mice, including the F4/80+ stainings (A) and their quantitation (B-C) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.

F4/80 immunostaining was used to detect the monocyte/macrophage infiltration condition in kidney tissues. As shown in FIGS. 7 (A), (B) and (C), after the $28^{th}$ day of disease induction, high level of monocyte/macrophage infiltration can be observed in glomerulus and the periglomerular region of interstitium. However, kidney tissues of the osthole treated mice showed significantly reduced infiltration, which is of similar level to that of the normal control group.

Figure 8:
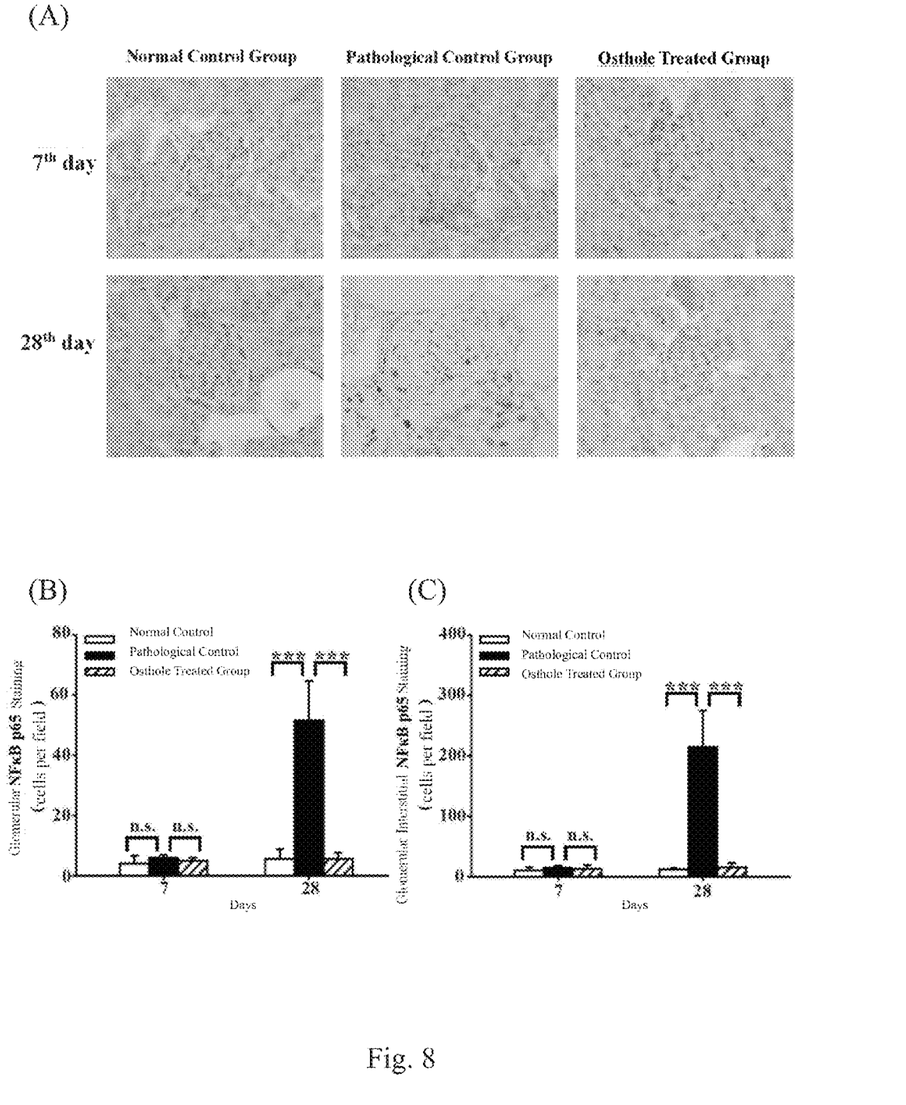
FIG. 8 shows the NF-κB expression level in kidney tissues of osthole treated FSGS mice, including the staining results (A) and their quantitation (B-C) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.

The NF-κ3 activation condition in kidney tissues was further examined by immunostaining. As shown in FIGS. 8 (A), (B) and (C), relative to the normal control group, after the $28^{th}$ day of disease induction, the pathological control group showed significant NF-κB p65 nuclear translocation, indicating the activation of the inflammatory response, which can be suppressed by osthole.

Figure 9:
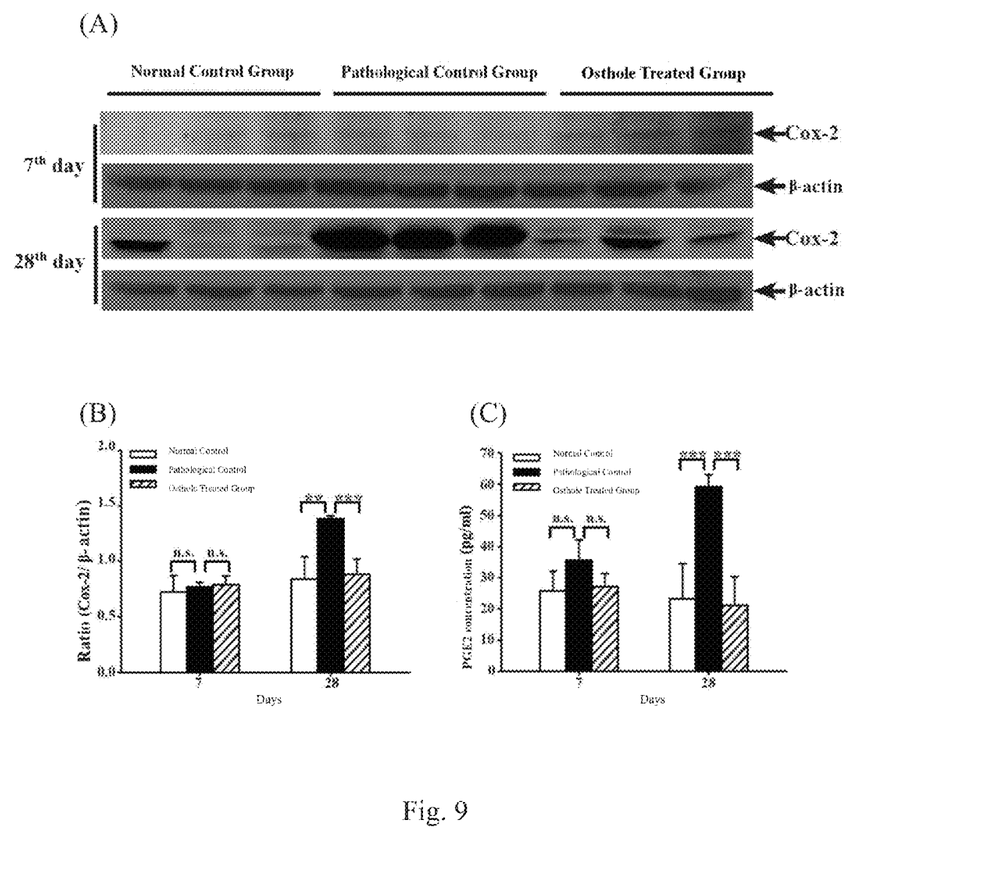
FIG. 9 shows the renal Cox-2 and serum PGE2 expression levels of osthole treated FSGS mice, including the Cox-2 Western blot analysis result (A) and its quantitation (B) and the PGE2 concentration assay (by ELISA) (C) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.

COX-2 and PGE2 protein expression were then analyzed to evaluate the inflammatory response in the kidney. As shown in FIGS. 9 (A), (B) and (C), after the $28^{th}$ day of disease induction, expression levels of COX-2 and PGE2 in pathological control group showed significant increase, while the expression levels of such proteins were reduced in osthole treated group, which were restored to levels similar to the normal control group.

These results show that osthole suppresses the inflammatory cell-infiltration and inflammatory responses in kidney tissues.

2.5 Osthole Suppresses Apoptosis in Kidney Tissue

Figure 10:
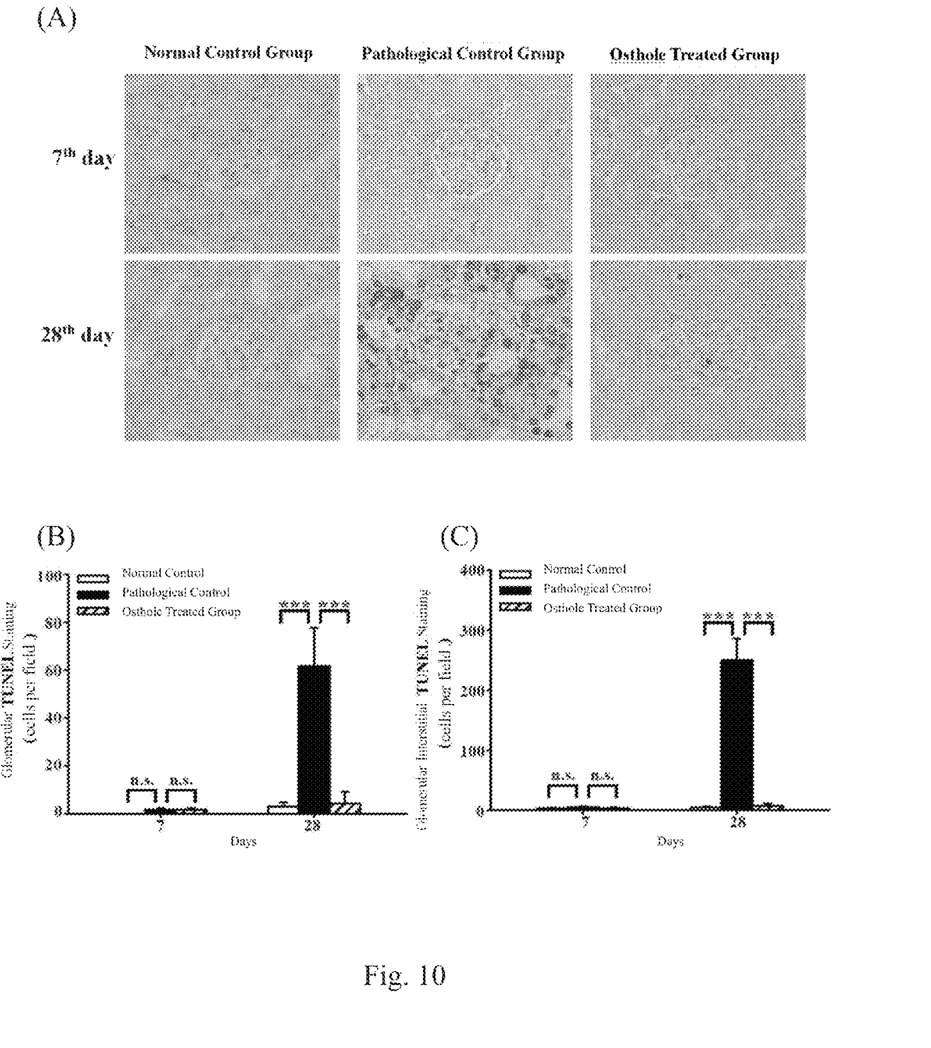
FIG. 10 shows the kidney tissue cell apoptosis conditions in osthole treated FSGS mice, including the staining results (A) and their quantitation (B-C) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.

Apoptosis in kidney tissue is known as one of the reasons to the exacerbation of FSGS, which is followed with the formation and sedimentation of extraglomerular matrix, causing a non-reversible physiological change. The effect of osthole on glomerular apoptosis is discussed below. TUNEL staining was used to evaluate the apoptosis condition in kidney tissues. FIGS. 10 (A), (B) and (C) show that after the $28^{th}$ day of disease induction, kidney tissues showed a great amount of apoptosis, which can be suppressed by administration of osthole, where the staining results of the kidney tissues is similar to that of the normal control group.

Figure 11:
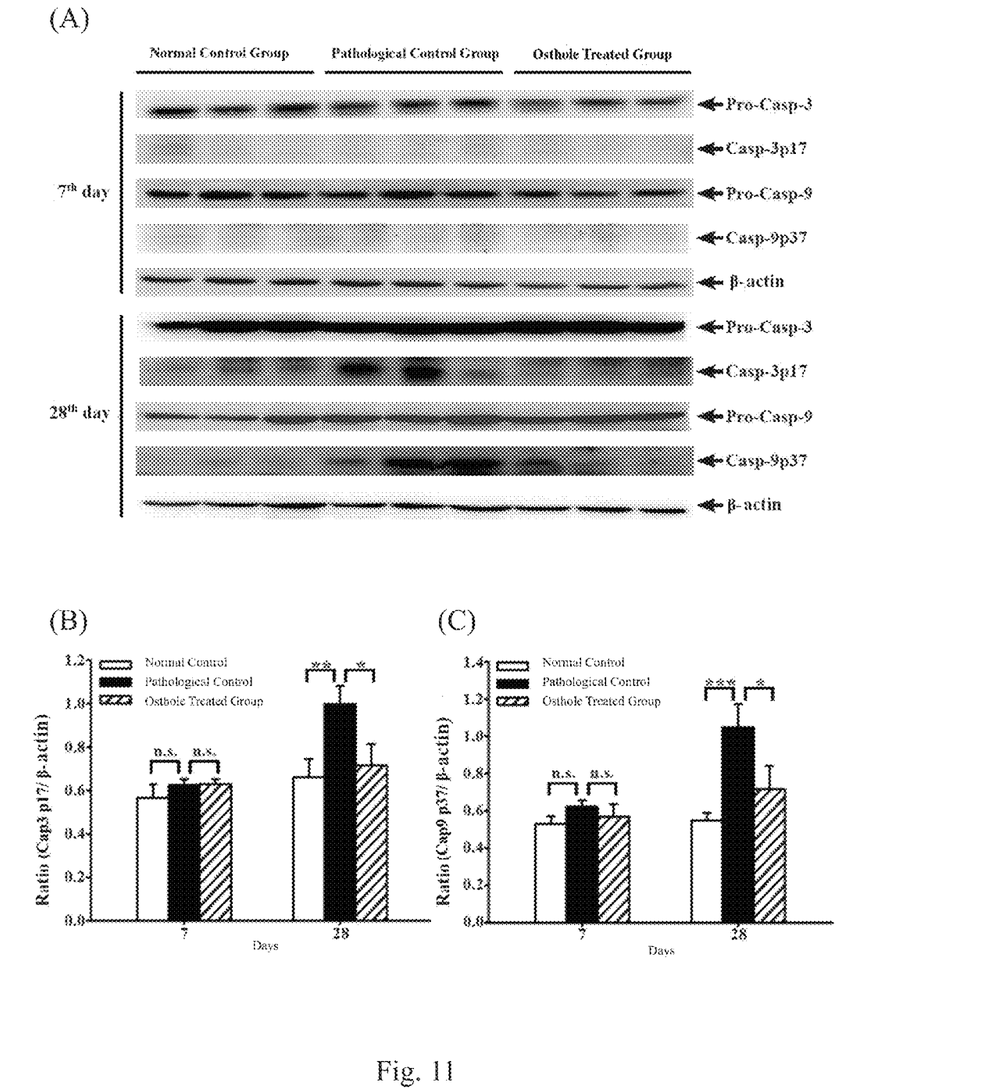
FIG. 11 shows the kidney tissue cell apoptosis pathway analysis result in osthole treated FSGS mice, including the Western blot analysis result of pro-caspase-3, pro-caspase-9, activated caspase-3 and activated caspase-9 (A) and the quantitation of activated caspase-3 and activated caspase-9 (B-C) of the normal control group, the FSGS disease group (pathological control group), and the FSGS disease osthole treatment group after the 7th and the 28th day of lesion induction. $*p<0.05$, $p<0.01$, $*p<0.005$, n.s.=non-significant.

The molecular mechanism of osthole suppression of apoptosis was further examined with Western blot analysis to detect the expression level of caspase-3, caspase-8 and caspase-9. The expression level of caspase-8 did not show significant difference (data not shown). The analysis results in FIGS. 11 (A), (B) and (C) showed that the caspase-3 and caspase-9 (p17 and p37 fragments) in activated state in the pathological control group increased following the progression of the disease, where the expression levels of such proteins can be suppressed significantly by the administration of osthole.

These results show that osthole reduces apoptosis by reducing the expression of the activated caspase-9 and caspase-3.

3. Conclusion

The present invention unexpectedly found that administering osthole to FSGS mice can significantly suppress the progression of the disease, including reduction of proteinuria, amelioration of kidney function, reduction of inflammatory cell-infiltration and tissue sclerosis and fibrosis. In the discussion of its mechanism, osthole is involved in reducing oxidative stress through Nrf2 and its downstream pathway, reducing inflammation by NF-κ3 and reducing apoptosis by lowering the level of caspase-9 and caspase-3.

Thus, the present invention suggests that osthole may have an excellent renoprotective effect of treating and ameliorating syndromes of FSGS. According to the present invention, osthole may be used as a medicament, which can be combined with medicaments that are presently available, to reduce the dosage and in turn the possible side effects.

It is generally believed that persons skilled in the art of the present invention should be able to utilize the present invention to its broadest scope based on the descriptions herein without further illustration. Therefore, it should be understood that the descriptions and claims provided herein are for illustration only but do not in any way limit the scope of the present invention.

What is claimed is:

1. A method for treating suppressing renal fibrosis in a subject afflicted with focal segmental glomerulosclerosis (FSGS), which comprises administering a therapeutically effective amount of an isolated osthole to the subject.

2. The method of claim 1, wherein the osthole is administered in an amount effective in reducing collagen IV expression in glomerular tissues in the subject.

3. The method of claim 1, wherein the osthole is administered in combination with one or more therapeutic agent for treating focal segmental glomerulosclerosis selected from the group consisting of corticosteroid drugs, non-steriodal anti-inflammatory drugs (NSAIDs), immunosuppressants, cytotoxic drugs and vasodilators.

* * * * *